(12) United States Patent
Chun et al.

(10) Patent No.: US 12,575,760 B2
(45) Date of Patent: Mar. 17, 2026

(54) CLOSED-LOOP WEARABLE SENSOR AND METHOD

(71) Applicant: Sibel Health Inc., Niles, IL (US)

(72) Inventors: Keum San Chun, Park Ridge, IL (US); Lian Yu, Glenview, IL (US); Matt Keller, Barrington, IL (US)

(73) Assignee: Sibel Health Inc., Niles, IL (US)

( * ) Notice: Subject to any disclaimer, the term of this patent is extended or adjusted under 35 U.S.C. 154(b) by 431 days.

(21) Appl. No.: 18/121,640

(22) Filed: Mar. 15, 2023

(65) Prior Publication Data

US 2023/0293047 A1      Sep. 21, 2023

Related U.S. Application Data

(60) Provisional application No. 63/321,737, filed on Mar. 20, 2022.

(51) Int. Cl.
    *A61B 5/11*        (2006.01)
    *A61B 5/00*        (2006.01)
    *G01P 13/00*       (2006.01)

(52) U.S. Cl.
    CPC .......... *A61B 5/1123* (2013.01); *A61B 5/4809* (2013.01); *A61B 5/6832* (2013.01); *A61B 5/7267* (2013.01); *A61B 5/7275* (2013.01); *A61B 5/7282* (2013.01); *A61B 5/7455* (2013.01); *A61B 5/746* (2013.01); *G01P 13/00* (2013.01); *A61B 2562/0204* (2013.01); *A61B 2562/0219* (2013.01)

(58) Field of Classification Search
    CPC ... A61B 5/1123; A61B 5/4809; A61B 5/6832;

A61B 5/7267; A61B 5/7275; A61B 5/7282; A61B 5/7455; A61B 5/746; A61B 2562/0204; A61B 2562/0219; G01P 13/00
    See application file for complete search history.

(56)                References Cited

U.S. PATENT DOCUMENTS

| | | |
|---|---|---|
| 10,551,935 B2 | 2/2020 | Valafar et al. |
| 2009/0312998 A1 | 12/2009 | Berckmans et al. |
| 2015/0335288 A1 | 11/2015 | Toth et al. |
| 2019/0150771 A1 | 5/2019 | Jeong et al. |
| 2021/0113099 A1* | 4/2021 | Rogers ................. A61B 5/4803 |
| 2021/0386300 A1* | 12/2021 | Rogers ............... A61B 5/02055 |

FOREIGN PATENT DOCUMENTS

| | | |
|---|---|---|
| WO | 2020264360 A1 | 12/2020 |
| WO | 2022094451 A1 | 5/2022 |
| WO | 2022216650 A1 | 10/2022 |

OTHER PUBLICATIONS

PCT/US2023/015686 International Search Report and Written Opinion of the International Searching Authority, dated Jul. 20, 2023, 2 pages.

* cited by examiner

*Primary Examiner* — Robert J Michaud
(74) *Attorney, Agent, or Firm* — Nolte Lackenbach Siegel

(57)                ABSTRACT

Methods and electronic devices for measuring motion and acoustic signatures of physiological processes of a human subject. The method includes measuring motion and acoustic signatures of physiological processes of a human subject; sending the first feature-related data to a machine learning service; sending the first feature-related data to a machine learning service; and determining a predicted detection of human scratching activity by the machine-learning service by performing a machine-learning operation on the feature-related data.

19 Claims, 7 Drawing Sheets

200

300

400

Feature related data

CLOSED-LOOP WEARABLE SENSOR AND METHOD

CROSS REFERENCE TO RELATED APPLICATIONS

The present application claims the benefit of and priority to U.S. provisional application No. 63/321,737, filed on Mar. 20, 2022, the content of which is hereby incorporated by reference as if set forth in its entirety herein.

TECHNICAL FIELD

Embodiments described herein generally relate to systems and methods for sensing physiological parameters and, more particularly but not exclusively, to systems and methods for detecting certain behavior based on physiological parameters.

BACKGROUND

More than 1 out of 10 people suffer from acute or chronic itch. While itch causes significant morbidity, there are no technologies that accurately, objectively, and continuously assess itch by quantifying scratch (or other physiological symptoms or activities) in a user's natural environment. Accordingly, therapeutic options remain limited.

Also, existing techniques rely on communicating sensor-obtained data to a remote location for analysis. This contributes to lag and a delay in analysis performance.

A need exists, therefore, for systems and methods that overcome the disadvantages associated with existing techniques.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to an electronic device for measuring motion and acoustic signatures of physiological processes of a human subject. The electronic device comprises an inertial measurement unit (IMU) for detecting the motion and acoustic signatures; a microcontroller unit (MCU) communicatively coupled to the IMU; wherein the IMU is operably in direct mechanical communication with the skin of the subject; wherein the MCU calculates feature-related data from the motion and acoustic signatures; wherein the MCU sends the feature-related data to a machine learning service executing on the MCU; and the machine-learning service predicts the detection of human scratching activity by the human subject by performing a first machine-learning operation on the feature-related data.

In some embodiments, the electronic device also comprises a vibratory motor for alerting the human subject. In some embodiments, the MCU turns on the vibratory motor when human scratching activity is detected.

In some embodiments, the MCU calculates a second-feature-related data from the motion and acoustic signatures. In some embodiments, the second feature-related data is used to determine the intensity of the detected scratching activity. In some embodiments, the second feature-related data is used to predict that the human subject is asleep. In some embodiments, a second machine learning operation is used to detect scratching activity if the subject is predicted to be asleep. In some embodiments, a pattern of vibratory motor operation is determined based on whether the subject is predicted to be asleep.

In some embodiments, the detection of human scratching activity comprises detecting a start of the scratching activity, associating time one with the start of the scratching activity, detecting an end of the scratching activity, and associating time two with the end of the scratching activity. In some embodiments, the MCU calculates a scratch duration by subtracting time one from time two.

According to another aspect, embodiments relate to a method. The method comprises measuring motion and acoustic signatures of physiological processes of a human subject; calculating a first feature-related data from the motion and acoustic signatures; sending the first feature-related data to a machine learning service; and determining a predicted detection of human scratching activity by the machine-learning service by performing a machine-learning operation on the feature-related data.

In some embodiments, a second feature-related data is calculated from the motion and acoustic signatures. In some embodiments, the second feature-related data is used to predict that the human subject is asleep.

In some embodiments, the method further includes providing haptic feedback to the human subject upon determining the predicted detection of human scratching activity.

In some embodiments, measuring the motion and acoustic signatures involves measuring the signatures by an inertial measurement unit, and determining the detection involves executing a microcontroller unit, wherein the inertial measurement unit and the microcontroller are located on the sensor.

In some embodiments, the machine learning operation includes at least one of a neural network, a logistic regression classifier, and a random forest classifier

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
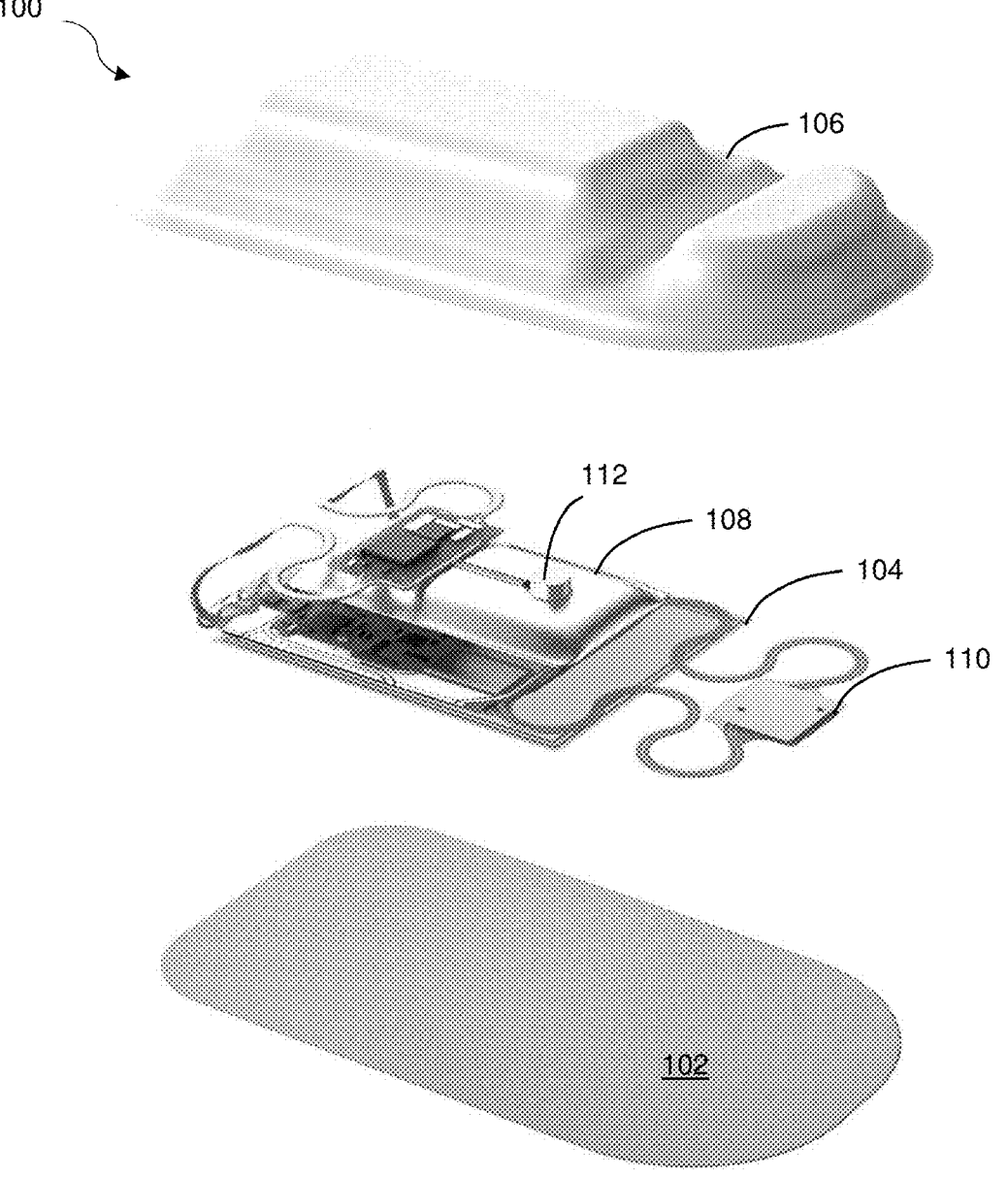
FIG. 1 illustrates a view of a sensor in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Pruritus, or more informally "itch," is a symptom common to several medical conditions. These conditions may range from dermatologic pathologies to systemic diseases such as, and without limitation, renal failure, urticaria, diabetes, chronic pruritus of the elderly, and malignancies like cutaneous T-cell lymphoma (CTCL).

Acute and chronic itch affects between 8% and 14% of the population, respectively, and can adversely affect quality of life. The itch-scratch cycle generally starts with an itch, which triggers scratch, which in turn causes further itch, inflammation, and infection.

This scratching behavior can become habitual. Habitual scratching can be particularly troublesome if scratching occurs during sleep, which is essential for proper developmental growth, physical growth, mental health, and general well-being. However, nighttime scratching may disrupt sleep quality and cause or at least contribute to the onset of sleep disorders.

Existing techniques for evaluating itch involve administering or otherwise providing patients with subjective surveys involving numeric grading scales. There is poor correlation between actual scratching activity behavior and observed scratching behavior, however. Additionally, results of these surveys may be of questionable value because different patients may have different tolerances or sensitivity to different severities of itch.

Another existing approach for evaluating itch involves direct visualization of scratching with video recordings. However, this is time-consuming, impractical, and intrusive to users.

Embodiments described herein provide novel systems and methods for evaluating itch, detecting scratching activity, and providing therapeutic biofeedback. FIG. 1 illustrates an acoustomechanic, wearable sensor device 100 in accordance with one embodiment. The sensor 100 may be operably positioned with respect to a person's skin to gather physiological data, behavior data, or the like. Specifically, the sensor 100 may capture low-frequency data corresponding to motion and high-frequency data corresponding to a wide variety of clinical biomarkers.

The sensor 100 may include a base portion 102, an electronics board 104, and a top portion 106. The bottom portion 102 may include or be configured as a waterproof, silicone portion that may attach to a user's hand or other body location. Additionally, the bottom portion 102 should be soft and flexible such that it can adapt to movements of the user's hand and remain in operable contact with the user's hand during movement. The bottom portion 102 may remain in operable contact with the user at least in part due to an adhesive.

In some embodiments, the base portion 102 may attach to dorsal side of a user's hand. For example, the base portion 102 may be positioned over the metacarpal bones associated with a user's index finger and middle finger. In this location, the sensor 100 may detect low and high frequency signals resulting from the user performing a scratching or rubbing motion with one or more of their fingers, wrist, hand, etc.

Upon predicting the detection of scratching activity (e.g., determining that a user is performing a scratching activity or at least likely performing a scratching activity), the sensor may provide haptic feedback to the user. This haptic feedback may alert the patient of the scratching activity (including unconscious scratching activity) to encourage the user to cease scratching.

The electronics board 104 may include or otherwise support several components. These may include but are not limited to a microcontroller, power source 108, accelerometer 110, a haptic feedback provider 112 such as a haptic motor, and wireless charging circuitry 114. The sensor 100 therefore provides multiple hardware components in a compact space to minimize the form factor and maximize usability and practicality of the device with low power consumption and longer operation.

The top portion 106 may be formed of or otherwise include a soft, stretchable, and water-proof material. The top portion 106 should also be able to flex to accommodate movement of the user's hand or other body portion.

Figure 2:
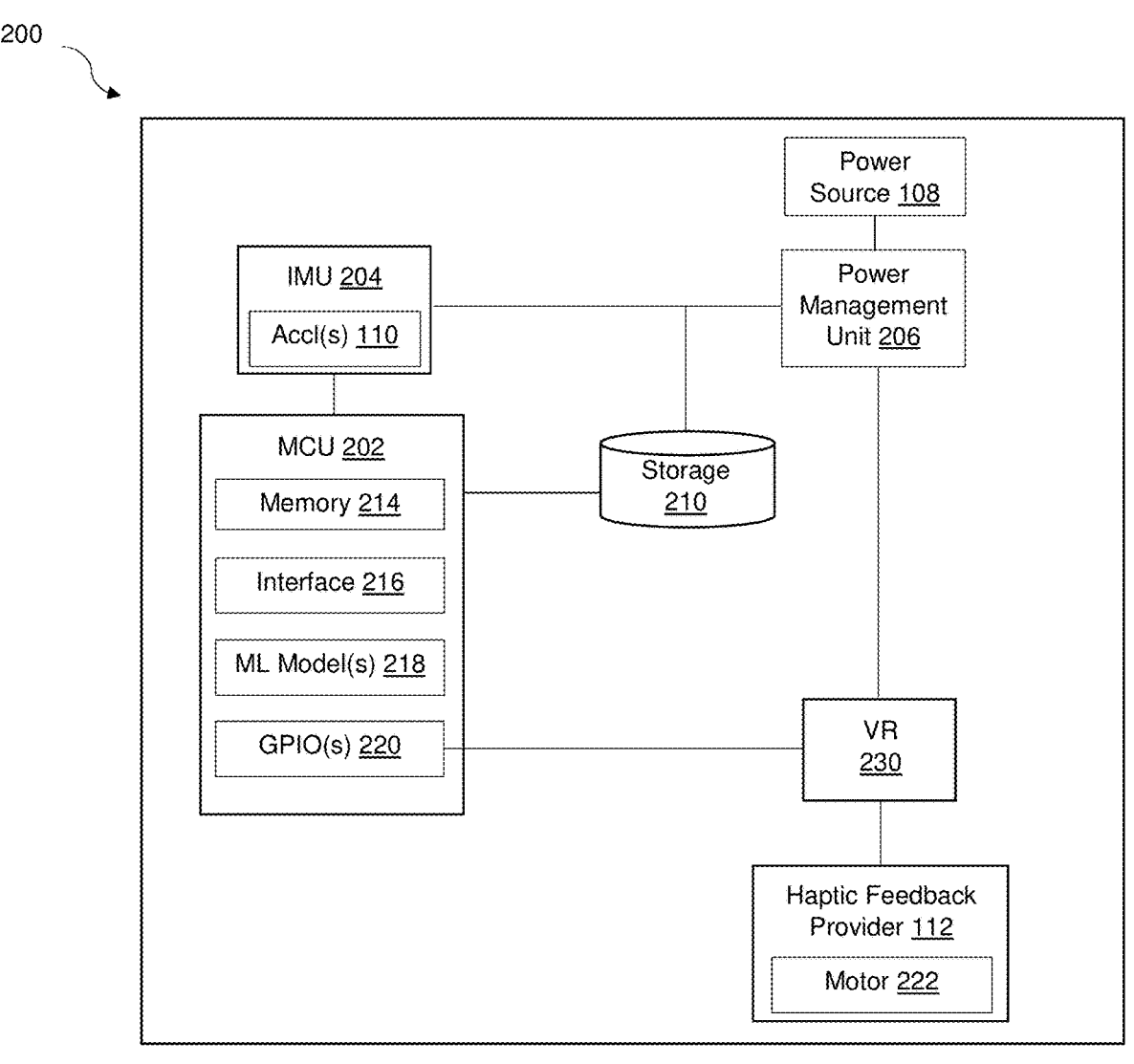
FIG. 2 presents a diagram of an electronics board of the sensor of FIG. 1in accordance with one embodiment.

FIG. 2 illustrates a diagram 200 of the electronics board 104 of FIG. 1 in accordance with one embodiment. Components shown in FIG. 1 are presented in FIG. 2 using the same reference numerals. The electronics board 104 in FIG. 2 may include a microcontroller unit (MCU) 202, an inertial measurement unit (IMU) 204, a power source 108, a power management unit (206), a storage 210, and a haptic feedback provider 212.

The MCU 202 may execute or otherwise include memory 214, an interface 216, one or more machine learning models 218, and general-purpose input-outputs (GPIO(s)) 220. The MCU 202 may be located on-board with the sensor 100 so that the required analytics are performed on the sensor 100.

The IMU 204 may include or otherwise execute one or more accelerometers 110. The accelerometer(s) 110 may measure acceleration along the x- and y-axes at 200 Hz. The accelerometer(s) 110 may measure acceleration in the z-axis up to 1,600 Hz. Acceleration in these directions may indicate movement such as scratching activity, for example.

The MCU 202 includes various combinations of resistors, transistors, and diodes to form any number of logic gates to execute appropriate programs. The MCU 202 may store any combination of types of memory 214 such as RAM memory configurations. The memory 214 may include non-volatile memory such as flash memory, EPROM, EEPROM, ROM, and PROM, or volatile memory such as static or dynamic RAM, as discussed above. The exact configuration/type of onboard memory 214 may of course vary as long as instructions for analyzing data from the IMU 204 may be performed by the MCU 202.

The machine learning model(s) 218 may execute one or more of a variety of machine learning models 218 to analyze data gathered by and provided from the IMU 204. One or more machine learning models 218 may have been trained on data from clinical studies monitoring scratching activity.

For example, data regarding scratching activity events may be collected from various body sites over a period of time. These body sites may include, but are not limited to, the dorsal hand, head, forearm, inner elbow, thigh, and calf. Non-scratching movements may also be considered during a training phase, and may include activities such as waving, texting, tapping, movements associated with restlessness, etc.

Upon detecting scratching activity, the GPIO(s) 220 may communicate a signal to the haptic feedback provider 212. The haptic feedback provider 212 may then provide haptic feedback to the user. The haptic feedback provider 112 may include an eccentric rotating mass (ERM) motor 222 to create vibrations.

In some embodiments, the motor 222 may be configured to rotate at 10,000 rpm to generate 1.4 G of vibratory feedback. Regardless of the exact amount of vibratory feedback provided, the vibratory feedback should be sufficient to alert users, even during sleep.

The haptic feedback provider 112 may be powered by a voltage regulator 230 that is controlled by the (GPIO) pin 220 from the MCU 202. For example, the voltage regulator 230 may use pulse width modulation to create feedback of variable strength, duration, or some combination thereof. Pulse width modulation utilizes pulses of varying widths to create a cycle that may modulate the rotation speed of the motor 222. Using this configuration, the haptic feedback provider 112 may generate several types of haptic profiles. For example, the haptic feedback provider 112 may generate profiles with gentle vibrations, intense vibrations, ramping effects, short bursts, etc.

The power source 108 may be any sort of power source to supply power to the components of the board 104. In some embodiments, the power source 108 may be a rechargeable Li-polymer or Li-ion batteries.

The storage 210 may store data regarding the user and signals appropriate for the user. For example, a particular user may require a haptic signal that is intense and in spurts to detect the haptic signal. Accordingly, the haptic profiles or otherwise the type of haptic feedback provided may vary and may depend on the user, the message intended to be conveyed, etc. For example, feedback may vary in length, intensity, pattern(s), or some combination thereof.

Similarly, users may select their most preferred haptic feedback to minimize aggravation or mitigate habituation. For example, some users may not notice or respond to a low-intensity vibration from the haptic feedback provider 212. Accordingly, some users may prefer to receive a higher intensity vibration.

Additionally or alternatively, some users may find high intensity vibrations jarring or disruptive. Accordingly, some users may prefer to receive a lower intensity vibration.

Data regarding sleeping patterns, scratching activity and other user behavior may have been previously gathered. As part of a training phase, a user wearing the sensor may have been asked to perform a scratching activity on a force sensor (not shown in FIG. 1).

For example, a user may wear the sensor and apply a scratching motion on a force resistive resister ("FSR"). The surface of the force sensor may be covered with an aluminum foil to make the coefficient of friction ("COF") of the surface similar to the dorsal hand ("DH"). The FSR may detect the force applied to its surface during the test scratching activity (i.e., while the user is scratching the surface of the FSR). As the user is wearing the sensor during the test scratching activity, the accelerometer of the sensor may simultaneously gather acceleration data related to the user's movement.

The applied force may represent an intensity level of the scratch activity. That is, the higher the detected force resultant from a scratch activity, the more intense the scratch activity.

Figure 3:
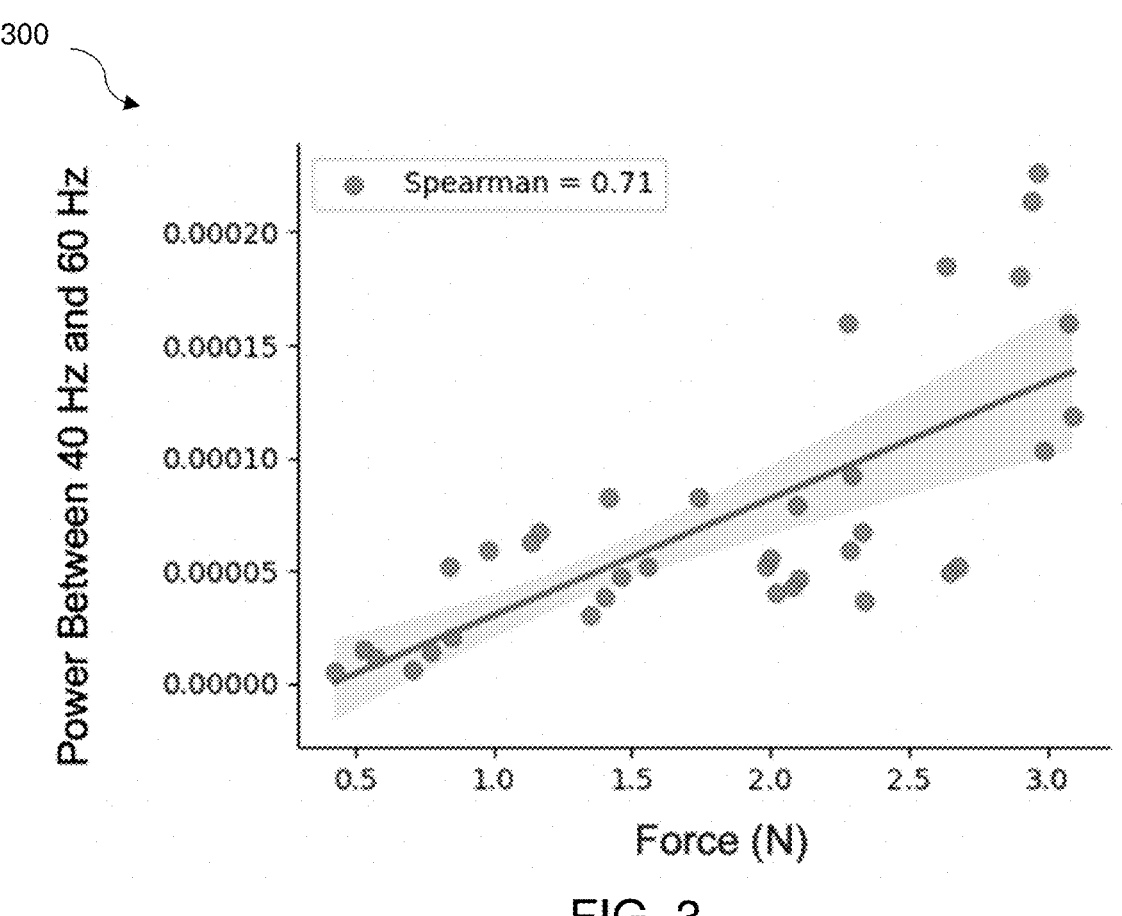
FIG. 3 presents a graphical representation of the relationship between force and scratch in accordance with one embodiment.

FIG. 3 presents a graph 300 showing the relationship between frequency and force. The graph 300 also illustrates the Spearman correlation to show the relationship between scratch intensity (measured in force (N)) and the sensor signal. For each trial, the speed of scratching and the angle between the finger and the surface of the FSR were maintained constant. The power of the scratch signal collected by the sensor can then be computed. As scratch intensities increase, the power of the signal between 40 Hz and 60 Hz would increase.

Figure 4:
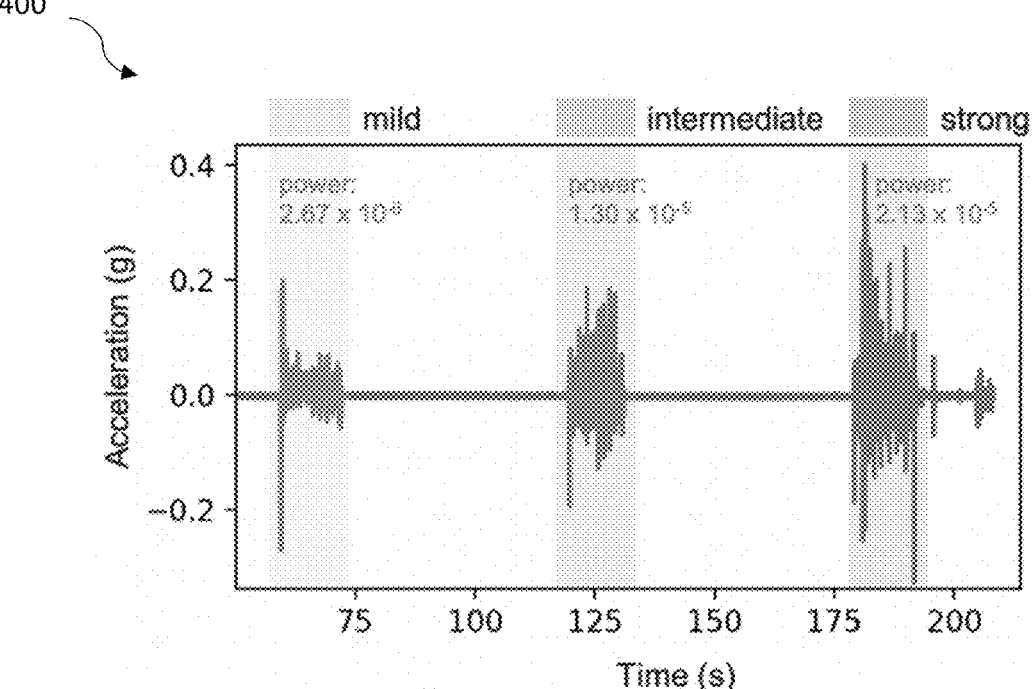
FIG. 4 presents a graphical representation of different scratching activities detected over a time period in accordance with one embodiment.

FIG. 4 presents a graphical representation 400 of different scratching activities detected over a time period. As seen in graphical representation 400, acceleration data of scratching activity of varying intensities is detected over a time period. As scratch intensities increase, the power of the signal between 40 Hz and 60 Hz would increase.

In operation, the IMU 204 may gather data regarding user activity. For example, and as discussed above, the accelerometer(s) 110 may gather acceleration data in various axes to identify behavior that may indicate scratching activity.

The machine learning model(s) 218 may execute one or more of a variety of machine learning models 218 to analyze data from the IMU 204. One or more machine learning models 218 may have been trained on data from clinical studies monitoring scratching activity.

For example, scratching activity training events may be collected from healthy individuals who are at least 18 years old and having no skin allergies to adhesive or current skin irritation near anticipated sensor sites to develop a machine learning algorithm. For detecting these scratching activity events, the sensor 100 may be placed on the dorsal hand of the participant along their second digit metacarpal bone using a skin adhesive. Each participant may perform scratching activities for 35 seconds and non-scratching activities for 65 seconds. The participants may perform multiple scratching activities over clothing (e.g., on their abdomen, thigh, calf, knee, and shoulder), and may perform multiple scratching activities directly on skin (e.g., on their cheek, head, inner elbow, outer elbow, forearm, back of hand, and palm).

The machine learning model(s) 218 may include one or more of random forest classifiers, logistic regression, neural networks, or the like. The exact type of machine learning model(s) 218 used may vary as long as they can analyze data from the IMU 204 to identify scratching activity.

Figure 5:
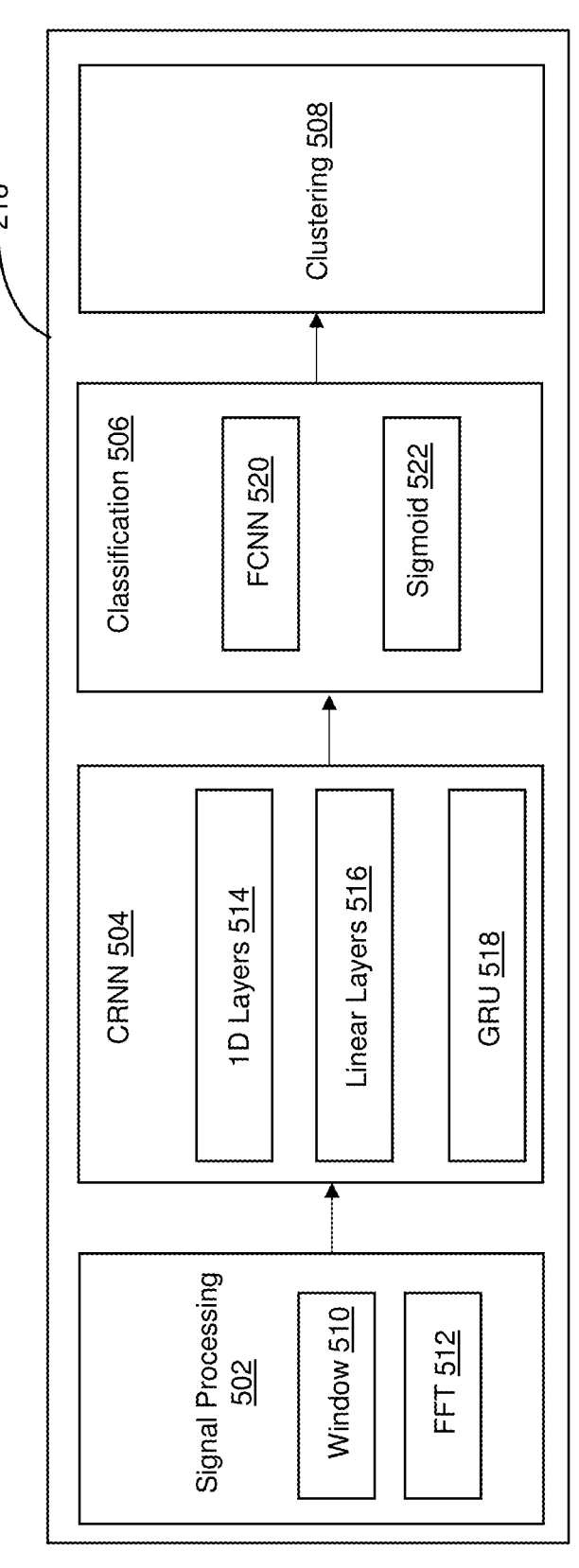
FIG. 5 illustrates a workflow for analyzing feature-related data in accordance with one embodiment.

FIG. 5 illustrates a workflow 500 for analyzing data from the IMU 204 in accordance with one embodiment. One or more machine learning models 218 may perform the workflow 500 or at least part of the workflow 500. The workflow 500 or at least part of the workflow 500 may be used to train one or more aspects of a machine learning model 218. This particular model may include a signal processing block 502, a convolutional recurrent neural network ("CRNN") 504, a classification module 506 and a clustering module 508.

Training data obtained from subjects performing scratching and non-scratching behaviors may first be sent to processing block 502. This may be z-axis acceleration data and a sliding window module 510 may divide the acceleration data into a plurality of groups. For example, in some embodiments, the raw time series data of z-axis acceleration may be segmented into 320-milisecond (512 data points) frames, using a window with 75% overlap between adjacent frames. A fast Fourier transform module 512 may then compute a short-time Fourier transform ("STFT") features.

The CRNN 504 may then receive and process these features through one or more 1-D convolutional layers 514, linear layers 516, and a gated recurrent unit ("GRU") 518 layer analyzing temporal patterns of signals.

The output of the of the CRNN 504 may then be provided to a fully connected neural network 520 for classification. For example, predicted outputs may be clustered using a Density-Based Spatial Clustering of Applications with Noise (DBSCAN) algorithm. For example, a sigmoid function 522 may classify activity as scratching activity or non-scratching activity depending on the associated feature data.

Figure 6:
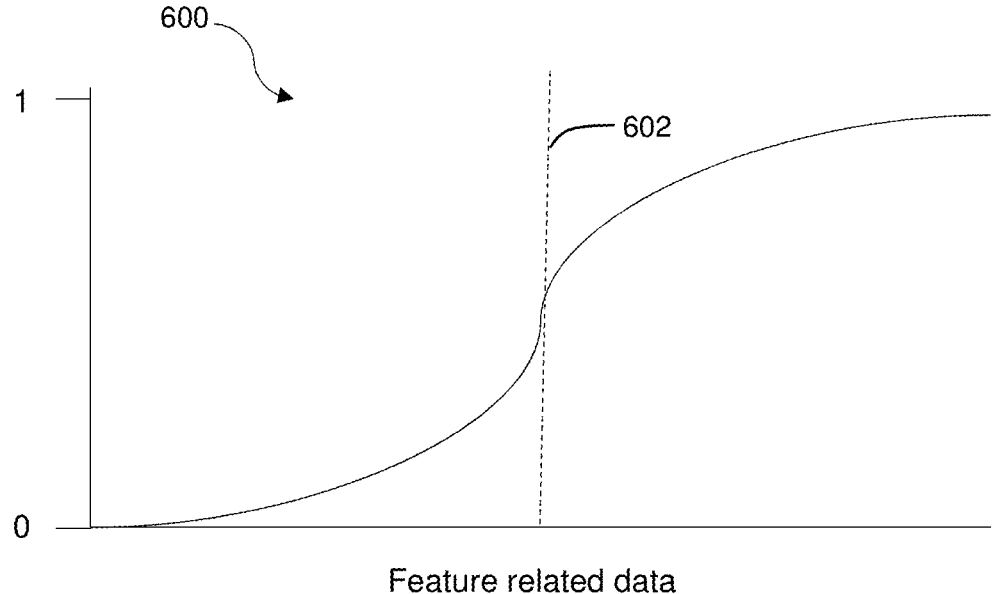
FIG. 6 illustrates a graphical representation of a sigmoid function in accordance with one embodiment.

FIG. 6 illustrates a graphical representation of a sigmoid function 600 in accordance with one embodiment. The sigmoid function 600 may represent a probability that particular activity, based on the feature related data on the x-axis, indicates scratching activity. The x axis may correspond to, for example, acceleration data obtained from the IMU 204.

A user or administrator (e.g., medical personnel) may specify a decision boundary 602 such that feature(s) that place activity to the right of the boundary 602 have a higher probability of being a scratching activity than being non-scratching activity. Accordingly, the classification module 506 may classify this activity as scratching activity.

In other words, the sigmoid function 600 represents the probability that particular activity, as determined by data from the IMU 204, represents scratching activity. Activity with features to the right of the boundary 602 may be classified as scratching activity, and activity with features to the left of the boundary 602 may be classified as non-scratching activity.

The workflow 500 may be used to classify activity at least substantially in real time. The sigmoid function 522 may then classify the activity as scratching or non-scratching based on output from the neural network. The clustering module 506 may then cluster the feature-related data by, for example, executing the DBSCAN algorithm.

As one aspect, the embodiments described herein allow for in-sensor computation of the CRNN model using edge computing. Based on the CRNN model developed, the sensor 100 may use a fixed size queue of 512 data points (320 milliseconds with 1,600 Hz sampling rate) may be defined to replicate the frames of the CRNN model. Once the queue is full, the data contained in the queue may be passed to the signal processing block to compute the STFT. The STFT may then be passed to the CRNN model. For every new incoming data point, the oldest data point is removed, and the new data point is added to the queue via a first in, first out (FIFO) scheme. Computation of scratch detection may be then repeated for every 128 new data points.

Figure 7:
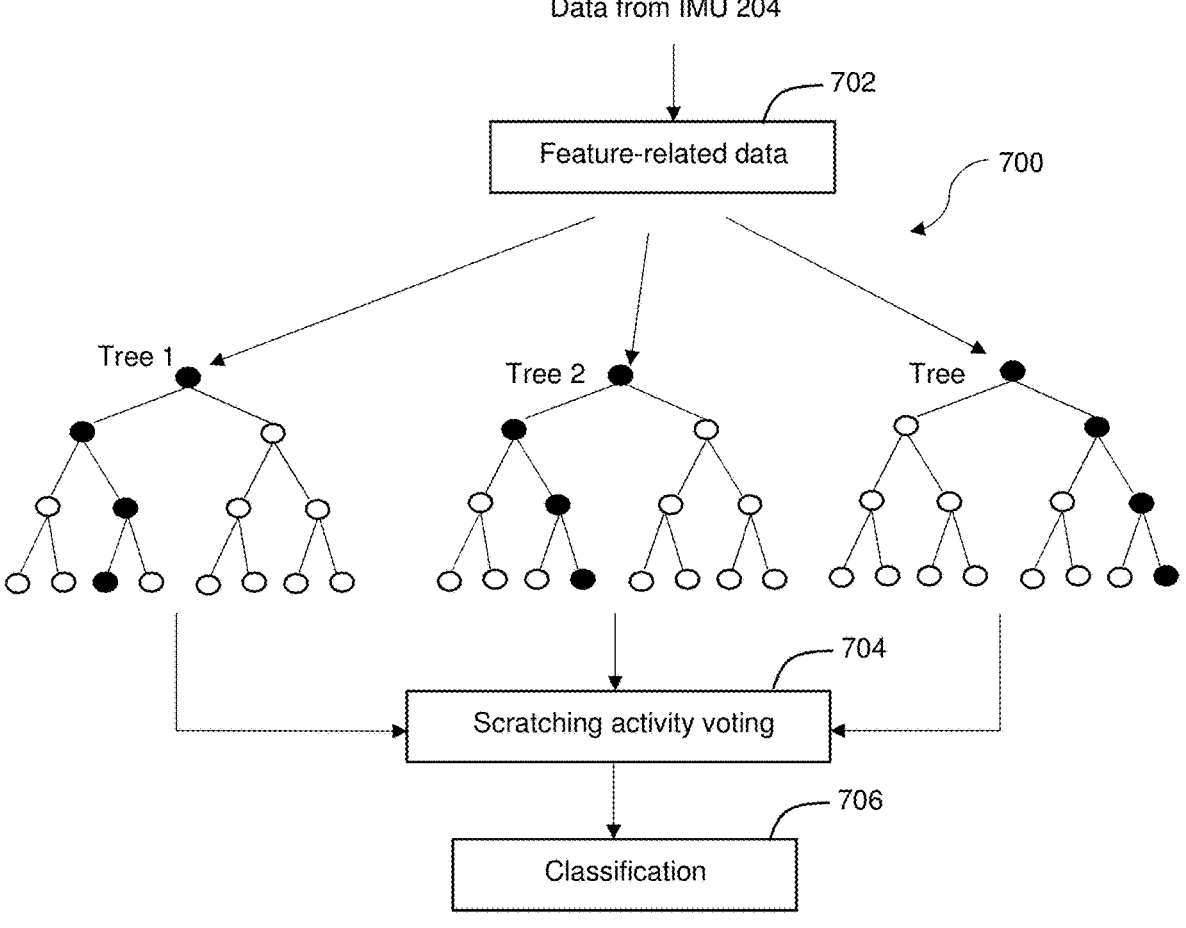
FIG. 7 illustrates a random forest classifier in accordance with one embodiment.

As another example, the embodiments herein may use random forest-based machine learning models to classify activity as scratching activity. For example, FIG. 7 illustrates a random forest classifier 700 that receives feature-related data from the IMU 204.

The random forest classifier 700 may include a plurality of trees that are each configured to detect whether some feature(s) are present or otherwise associated with identified activity. For example, tree 1 may first consider whether activity such as acceleration in the z axis above some threshold is detected (e.g., whether the user is likely sleeping, whether the acceleration occurred a threshold number of times, etc.). If so, the classifier 700 may traverse a certain branch of the tree Certain nodes of the trees are darkened indicating the presence or absence of some particular feature. Although three trees are illustrated in FIG. 7, any number of trees may be used to consider any number of features.

Each tree may output a classification decision regarding whether the activity is predictive of scratching activity. These predictions are based on the presence or absence of certain features.

The classification decisions of one or more trees may be combined in step 704. A classification decision is then provided in step 706.

The above-discussed examples and illustrations of machine learning models are exemplary. Other types of machine learning models may be used, such as support vector machines, logistic regression-based models, or the like.

Referring back to FIG. 2, upon detecting scratching activity, the GPIO(s) 220 may issue a signal to the haptic feedback provider 212 to provide haptic feedback to the user. For example, the motor 222 may cause the sensor 100 to vibrate with some form, intensity, duration, or the like.

The user may detect or feel this vibration, which they may associate with scratching activity. For example, the vibration may remind the user they are scratching themselves, and may encourage the user to cease scratching.

As discussed above, the user may be sleeping while wearing the sensor 100. During sleep, the user may subconsciously scratch themselves. The sensor may nonetheless provide this haptic feedback, which may encourage the user to, albeit at least partially subconsciously, cease the scratching activity.

Figure 8:
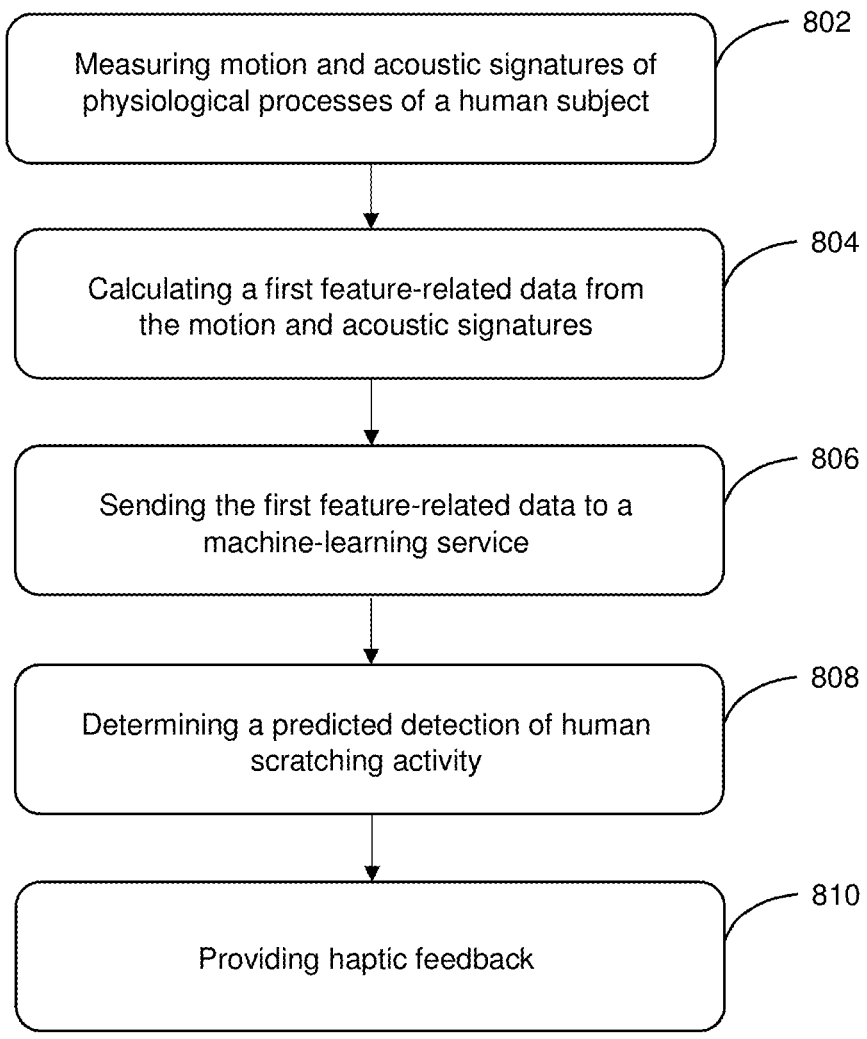
FIG. 8 depicts a flowchart of a method for monitoring user activity in accordance with one embodiment.

FIG. 8 depicts a flowchart of a method 800 for monitoring user activity in accordance with one embodiment. The sensor 100 of FIG. 1 or components thereof may perform one or more of the steps of method 800.

Step 802 involves measuring motion and acoustic signatures of physiological processes of a human subject. A human subject (for simplicity "user") may have been diagnosed with a medical condition for which itch is a symptom. Accordingly, the user may have a tendency or desire to scratch one or more locations on their body. As discussed previously, the scratching may exacerbate the symptom or condition.

The user need not have been diagnosed, either. Rather, the user may want to curb their scratching activity on their own, even without a diagnosis from medical personnel.

The user may place a sensor such as the sensor 100 on a location of their body, such as on their dorsal hand between the second and third metacarpal bones. Alternatively, medical personnel may place the sensor on the user.

The sensor may continuously measure motion and acoustic signatures of physiological processes of a human subject, such as during sleep, during a medical examination, or the like. For example, the user may want to be deterred from performing scratching activity during sleep.

Step 804 involves calculating a first feature-related data from the motion and acoustic signatures. An MCU such as the MCU 202 of FIG. 2 may analyze received raw data regarding motion and acoustics associated with the user.

Step 806 involves sending the first feature-related data to a machine learning service. The machine learning service may include any of the types of models discussed previously, as well as any other type of model available now or formulated hereafter.

Step 808 involves determining a detection of human scratching activity by the machine learning service by performing a machine learning operation on the feature-related data. Step 808 may involve executing one or more machine learning models to determine whether the feature-related data indicates or at least suggests that the user is performing a scratching activity. For example, the machine learning model(s) may rely on previously-gathered data associated with known scratching activity.

Upon detecting scratching activity, step 810 involves providing haptic feedback to the user to encourage them to cease the scratching activity-whether they are sleeping or are awake. Accordingly, the embodiments herein provide a therapeutic biofeedback tool for itch.

The application of low-power, high fidelity, AI-based analytics integrated into epidermal sensors with skin-friendly adhesives such as with the sensor 100 for long-term wear maximizes clinical potential and relevancy. The integration of machine learning analytics with haptic feedback on the sensor 100 provides a closed loop modality to quantify scratch events and provide real-time accurate feedback to improve patient outcomes. This technology can serve as a platform to classify and provide feedback to patients suffering from a wide array of dermatological disorders and co-morbidities and to help guide and assess efficacy of treatment plans.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. An electronic device for measuring motion and acoustic signatures of physiological processes of a human subject, comprising:

a top portion;

a bottom portion;

an electronics board disposed between the top portion and the bottom portion;

a machine learning service disposed on the electronics board, the machine learning service including a trained and programmed machine language model to receive feature-related data and to generate a predicted detection of scratching activity by performing a machine-learning operation, the machine-learning operation including at least one neural network flow:

an inertial measurement unit (IMU) for detecting the motion and acoustic signatures, the IMU mounted on the electronics board and operably in direct mechanical communication with the skin of the subject;

a microcontroller unit (MCU) mounted on the electronics board and communicatively coupled to the IMU, the MCU to calculate feature-related data from the motion and acoustic signatures and send the feature-related data to the machine learning service executing on the MCU;

wherein the predicted detection of human scratching activity by the human subject is performed by a first machine-learning operation on the feature-related data using the trained and programmed machine language model, the first machine-learning operation involving the at least one neural network flow.

2. The device of claim 1, wherein the electronic device also comprises a vibratory motor for alerting the human subject.

3. The device of claim 2, wherein the MCU turns on the vibratory motor when human scratching activity is detected.

4. The device of claim 1, wherein the MCU calculates a second-feature-related data from the motion and acoustic signatures.

5. The device of claim 4, wherein the second feature-related data is used to predict that the human subject is asleep.

6. The device of claim 5, wherein a second machine learning operation is used to detect scratching activity if the subject is predicted to be asleep.

7. The device of claim 5, wherein a pattern of vibratory motor operation is determined based on whether the subject is predicted to be asleep.

8. The device of claim 1, wherein the detection of human scratching activity comprises detecting a start of the scratching activity, associating time one with the start of the scratching activity, detecting an end of the scratching activity, and associating time two with the end of the scratching activity.

9. The device of claim 8, wherein the MCU calculates a scratch duration by subtracting time one from time two.

10. The device of claim 4, wherein the second feature-related data is used to determine the intensity of the detected scratching activity.

11. The device of claim 1, wherein the at least one neural network comprises at least one of a convolutional recurrent neural network ("CRNN") and a fully connected neural network ("FCNN").

12. The device of claim 1, wherein a sigmoid function in the workflow classifies the human scratching activity differently from a human non-scratching activity.

13. The device of claim 1, wherein an accelerometer of the IMU measures the motion and acoustic signatures at a frequency greater than 150 Hz.

14. The device of claim 1, wherein an accelerometer of the IMU measures acceleration in a z-direction at a different frequency from acceleration in at least one of an x-direction and a y-direction.

15. A method, comprising:

providing a sensor including an inertial measurement unit (IMU) and a microcontroller unit (MCU) co-mounted on an electronics board and communicatively coupled to each other and including a machine learning service;

measuring motion and acoustic signatures of physiological processes of a human subject solely through the IMU;

calculating a first feature-related data from the motion and acoustic signatures;

sending the first feature-related data to a machine learning service; and determining a predicted detection of human scratching activity by the machine-learning service by performing a machine-learning operation using a machine language model of the machine learning service on the feature-related data, the machine-learning operation involving at least one neural network.

16. The method of claim 15, wherein a second feature-related data is calculated from the motion and acoustic signatures.

17. The method of claim 16, wherein the second feature-related data is used to predict that the human subject is asleep.

18. The method of claim 15 further comprising providing haptic feedback to the human subject upon detecting human scratching activity.

19. The method of claim 15 wherein the machine learning operation further includes at least one of a logistic regression classifier, and a random forest classifier.

* * * * *